(12) United States Patent
Terwey

(10) Patent No.: US 9,763,652 B2
(45) Date of Patent: *Sep. 19, 2017

(54) DISENGAGABLE CAM SYSTEM FOR TISSUE PUNCTURE CLOSURE DEVICE AND METHODS

(71) Applicant: TERUMO PUERTO RICO, L.L.C., Caguas, PR (US)

(72) Inventor: Russell D. Terwey, St. Michael, MN (US)

(73) Assignee: TERUMO PUERTO RICO, L.L.C., Caguas, PR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/181,060

(22) Filed: Jun. 13, 2016

(65) Prior Publication Data

US 2016/0287231 A1 Oct. 6, 2016

Related U.S. Application Data

(63) Continuation of application No. 13/817,331, filed as application No. PCT/US2011/001444 on Aug. 17, 2011, now Pat. No. 9,364,207.

(60) Provisional application No. 61/378,346, filed on Aug. 30, 2010.

(51) Int. Cl.
*A61B 17/08* (2006.01)
*A61B 17/00* (2006.01)
*A61B 17/04* (2006.01)

(52) U.S. Cl.
CPC ...... *A61B 17/0057* (2013.01); *A61B 17/0482* (2013.01); *A61B 17/0483* (2013.01); *A61B 2017/00623* (2013.01); *A61B 2017/00654* (2013.01); *A61B 2017/00659* (2013.01); *A61B 2017/00663* (2013.01)

(58) Field of Classification Search
CPC ............ A61B 17/0057; A61B 17/0482; A61B 17/0483; A61B 2017/00623; A61B 2017/00654
See application file for complete search history.

(56) References Cited

U.S. PATENT DOCUMENTS

| 6,045,569 A | 4/2000 | Kensey et al. |
|---|---|---|
| 6,090,130 A | 7/2000 | Nash et al. |
| 7,618,436 B2 | 11/2009 | Forsberg |

(Continued)

OTHER PUBLICATIONS

PCT International Search Report for International Application No. PCT/US2011/001444, mailed Nov. 8, 2011.

*Primary Examiner* — Ashley Fishback
(74) *Attorney, Agent, or Firm* — Buchanan Ingersoll & Rooney PC

(57) ABSTRACT

A method and apparatus for sealing a puncture or incision formed percutaneously in a tissue. The apparatus includes an anchor, a sealing plug, a suture, a compaction member assembly, a spool assembly, and a release member. The suture is positioned between the sealing plug and the anchor. The compaction member assembly is structured and arranged to apply an compressive force to compact the sealing plug toward the anchor. The spool assembly includes a plurality of post members, and the suture is wound about the post members to define a suture cam path. Unspooling the suture along the suture cam path provides driving of the compaction member assembly. The release member is operable to move the post members to release the suture member from the spool assembly.

20 Claims, 14 Drawing Sheets

(56) References Cited

U.S. PATENT DOCUMENTS

| | | |
|---|---|---|
| 7,618,438 B2 | 11/2009 | White et al. |
| 2005/0085851 A1 | 4/2005 | Fiehler et al. |
| 2006/0229673 A1 | 10/2006 | Forsberg |
| 2006/0229674 A1 | 10/2006 | Forsberg |
| 2006/0265006 A1 | 11/2006 | White et al. |
| 2007/0032823 A1 | 2/2007 | Tegg |

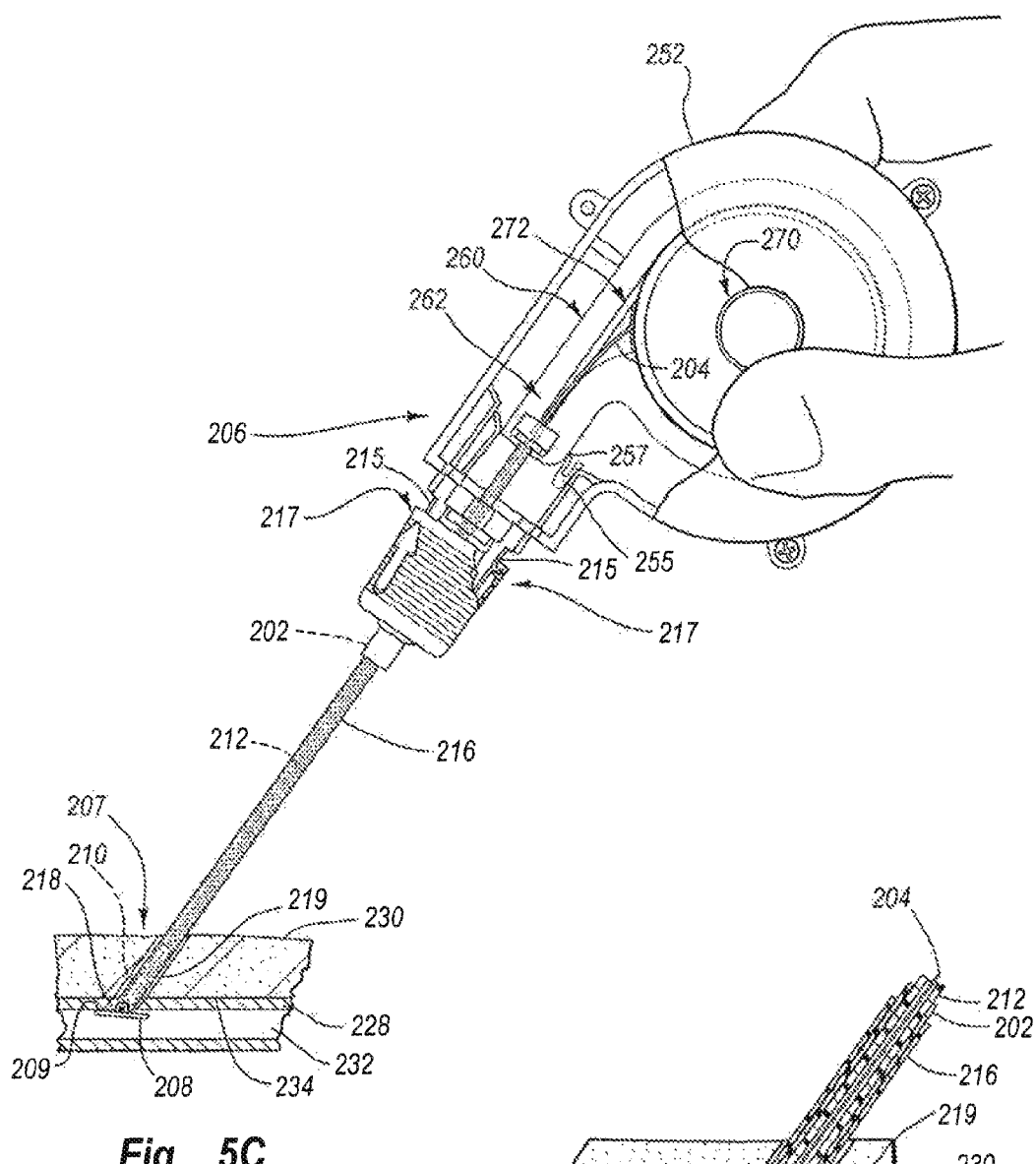
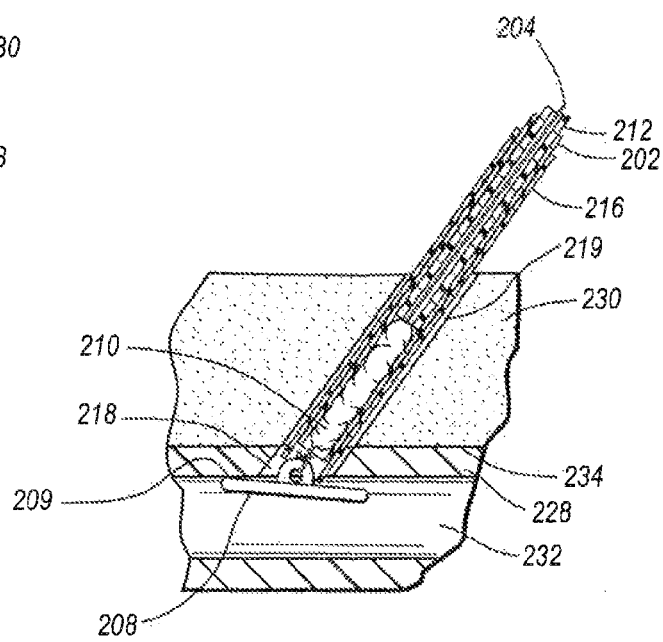
Fig. 5C
Fig. 5D

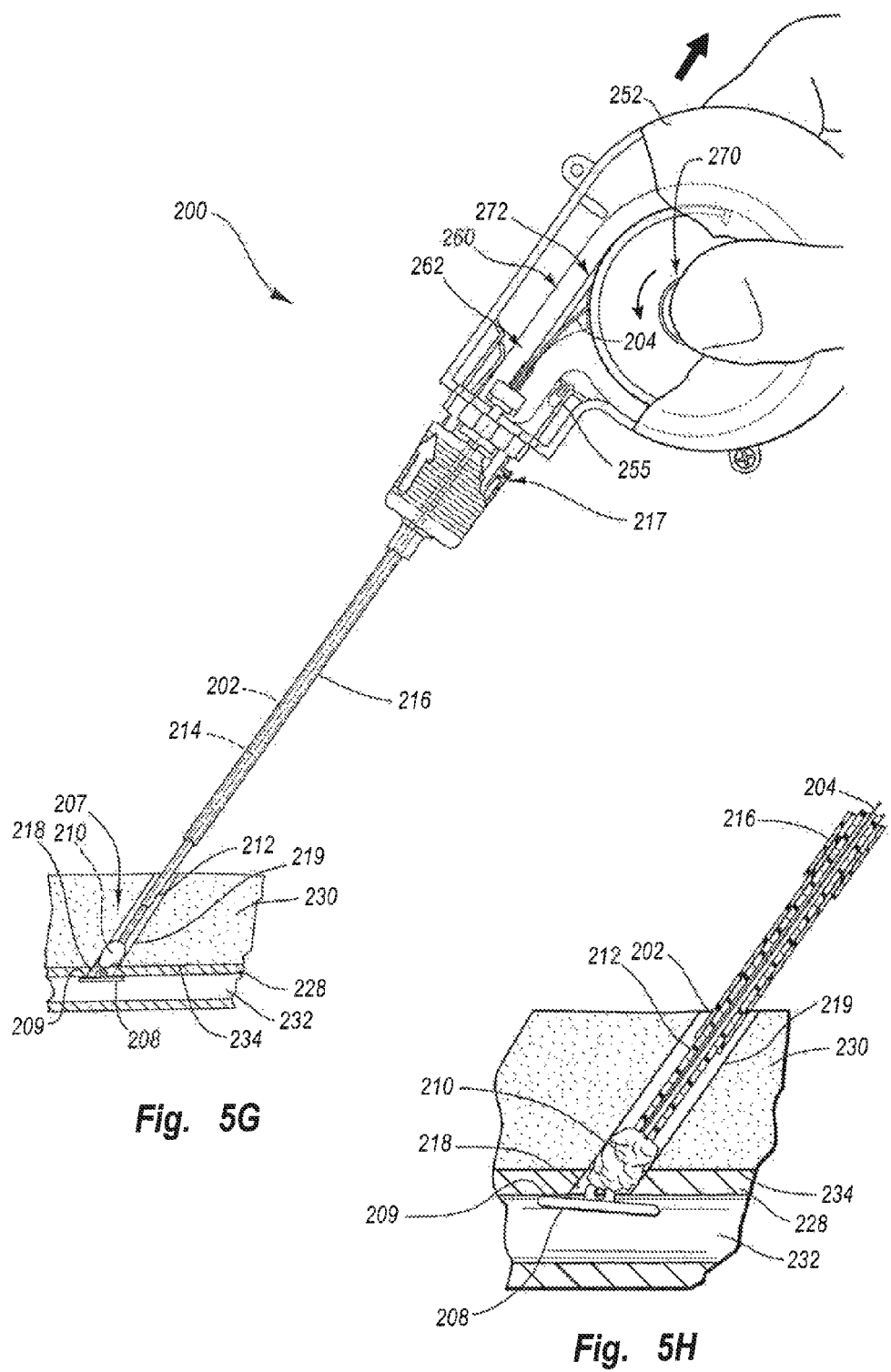

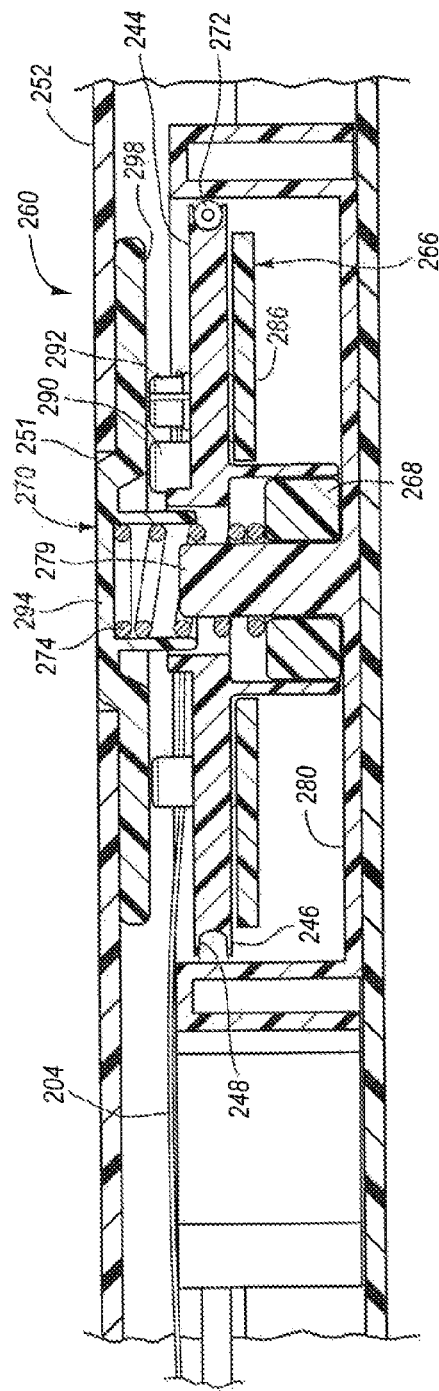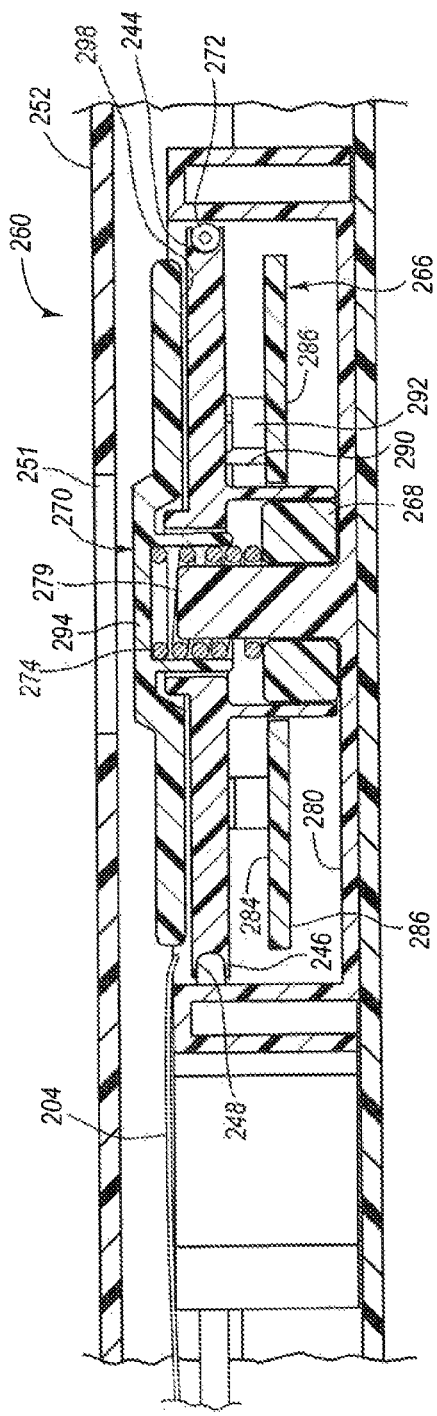

DISENGAGABLE CAM SYSTEM FOR TISSUE PUNCTURE CLOSURE DEVICE AND METHODS

RELATED APPLICATIONS

This is a continuation of U.S. patent application Ser. No. 13/817,331, filed 15 Feb. 2013 (with a 371(c) date of 7 May 2013), now pending, which is a 371 of PCT App. No. PCT/US2011/001444, filed 17 Aug. 2011, which claims the benefit of Provisional App. No. 61/378,346, filed 30 Aug. 2010, the disclosures of which are incorporated, in their entireties, by this reference

TECHNICAL FIELD

The present disclosure relates generally to medical devices and more particularly to devices for sealing punctures or incisions in a tissue wall.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing tissue puncture closure devices, such as those described in U.S. Pat. Nos. 6,090,130 and 6,045,569, which are hereby incorporated in their entireties herein by this reference.

Typical closure devices such as the ones described in the above-mentioned patents place a sealing plug at the tissue puncture site. Successful deployment of the sealing plug, however, requires that it be manually ejected from within a device sheath and tamped down to an outer surface of the tissue puncture using a compaction tube. The compaction procedure cannot commence until the device sheath (within which the compaction tube is located) has been removed so as to expose the compaction tube for manual grasping. Under certain conditions, removal of the sheath prior to compacting the sealing plug may cause the sealing plug itself to be displaced proximally from the tissue puncture, hindering subsequent placement of the sealing plug, and resulting in only a partial seal and associated late bleeding from the tissue puncture. Accordingly, there is a need for improving the mechanism for deployment of the sealing plug at the site of a tissue puncture.

SUMMARY

The present disclosure meets the above-described needs and others. Specifically, the present disclosure provides methods and systems for closing internal tissue punctures. However, unlike prior systems, the present disclosure provides automatic compaction to a sealing plug as the closure device is retracted. In addition, the present disclosure allows the automatic compaction system to disengage, facilitating full retraction of the closure device and easy separation of the sealing plug from the remainder of the closure device.

In one of many possible embodiments, the present disclosure provides a tissue puncture closure device that includes an anchor, a sealing plug, a suture, a compaction member, a spool assembly, and a release member. The compaction member assembly is structured and arranged to apply an axially directed compressive force to compact the sealing plug toward the anchor. The spool assembly includes a plurality of post members. The suture is wound about the post members to define a suture cam path. Unspooling the suture along the suture cam path provides driving of the compaction member assembly. The release member is operable to move the post members to release the suture from the post members after driving of the compaction member assembly.

The compaction member assembly may include a compaction tube and a coil, wherein the coil is structured and arranged to apply an axially directed compressive force to the compaction tube to drive the compaction tube to automatically compact the sealing plug toward the anchor. The plurality of post members may include at least four post members.

The tissue puncture closure device may further include a driving plate that is connected to the spool assembly. The driving plate may be configured to apply a force to the compaction member assembly to advance the compaction member assembly. The post members may extend through the driving plate. The driving plate may be connected to the spool assembly and include a recess having a contoured shape. At least a portion of the coil may be positioned in the recess.

The tissue puncture closure device may further include a housing within which the spool assembly is positioned, wherein a portion of the release member is exposed outside of the housing. The release member may be movable in a direction parallel with an axis of rotation of the spool assembly. The release member may move the post members in a direction parallel with an axis of rotation of the spool assembly. The driving plate may include a drive member arranged to contact a proximal end of the compaction member assembly.

The tissue puncture closure device may further include a roller bearing and a housing, wherein the spool assembly and driving plate are connected together and rotatable within the housing about the roller bearing. The tissue puncture closure device may further include an automatic driving assembly that includes the spool assembly, the compaction member assembly, the release member, a driving plate connected to the spool assembly, and a base, wherein the base is slidable within the housing.

Another aspect of the present disclosure relates to a tissue puncture closure device for partial insertion into and sealing of a tissue puncture in an internal tissue wall accessible through a percutaneous incision. The tissue puncture closure device includes an anchor, a sealing plug, a suture, a compaction member assembly, a storage spool, and a release member. The anchor is disposed on a distal side of the internal tissue wall. The sealing plug is disposed on a proximal side of the internal tissue wall. The suture is connected to and anchored at a distal end to the anchor and sealing plug. The sealing plug is slidable and cinchable along the suture toward the anchor to close the tissue puncture. The compaction member assembly is arranged to drive the sealing plug along the suture distally towards the anchor. The storage spool includes a plurality of movable posts onto which a proximal end of the suture is wound. The release member is operable to move the posts to release the suture from the storage spool.

The tissue puncture closure device may further include a driving plate connected to and arranged coaxially with the storage spool. The driving plate is configured to contact the compaction member assembly to advance the compaction member assembly. The tissue puncture closure device may also include a housing within which the storage spool is housed, wherein the release member includes a first portion accessible from outside of the housing and a second portion that extends into the housing to move the posts.

The tissue puncture closure device may include a driving plate configured to advance the compaction member assembly, wherein the driving plate includes a stop member arranged to contact a proximal end of the compaction member assembly. The posts may be configured to move in a direction parallel with a rotation axis of the storage spool. The posts may be arranged to provide a cam shaped path for the suture wound thereon.

Another aspect of the present disclosure relates to a method of sealing a tissue puncture in an internal tissue wall of a vessel accessible through a percutaneous incision. The method include providing a closure device having an anchor, a sealing plug, a suture secured between the sealing plug and the anchor, a compaction member assembly, a spool assembly having a plurality of movable post members arranged with a portion of the suture wound thereon, and a release member. The method further includes inserting the anchor through the tissue puncture and withdrawing the closure device from the tissue puncture with the anchor positioned within the vessel, wherein withdrawing the closure device rotates the spool assembly to drive the compaction member assembly to compact the sealing plug toward the anchor. The method also includes actuating the release member to release the suture from the post members.

The method may further include providing a driving plate connected to the spool assembly, wherein a distal end of the compaction member assembly is disposed adjacent the sealing plug, a proximal end of the compaction member assembly is in contact with the driving plate, and the post members extend through the driving plate, wherein actuating the release member moves the spool assembly relative to the driving plate. The method may further include a driving plate connected to the spool assembly, wherein the driving plate is configured to contact the compaction member assembly, and actuating the release member includes moving the post members relative to the driving plate.

The method may also include a housing and a bearing, wherein the spool assembly is mounted within the housing and rotatable about the bearing, and the method includes rotating the spool assembly within the housing to drive the compaction member assembly. The post members may be arranged to provide a cam shaped path for the portion of the suture wound thereon, and withdrawing the closure device unwinds the suture from the post members to apply a variable compaction force to the compaction member assembly.

Additional advantages and novel features will be set forth in the description which follows or can be learned by those skilled in the art through reading these materials or practicing the examples disclosed herein.

BRIEF DESCRIPTION OF THE DRAWINGS

The accompanying drawings illustrate various embodiments of the present disclosure and are a part of the specification. The illustrated embodiments are merely examples and do not limit the scope of the invention.

FIG. 5C is a side view of the tissue puncture closure device of FIG. 5A inserted through a procedure sheath and tissue puncture and engaged with a vessel in a first position.

FIG. 5D is a detailed inset of FIG. 5C.

FIG. 5G is a side view of the tissue puncture closure device of FIG. 5A engaged with a vessel in a third fourth position with a carrier tube retracted to expose a sealing plug adjacent to the tissue puncture and the sealing plug being compacted.

FIG. 5H is a detailed inset of FIG. 5G.

FIG. 8 is a cross-sectional view of the compaction assembly of FIG. 6 in a rest position.

FIG. 9 is a cross-sectional view of the compaction assembly of FIG. 6 with a release button activated to disengage the suture from the cam feature of the compaction assembly.

Throughout the drawings, identical reference numbers designate similar, but not necessarily identical, elements.

DETAILED DESCRIPTION

Figure 1:
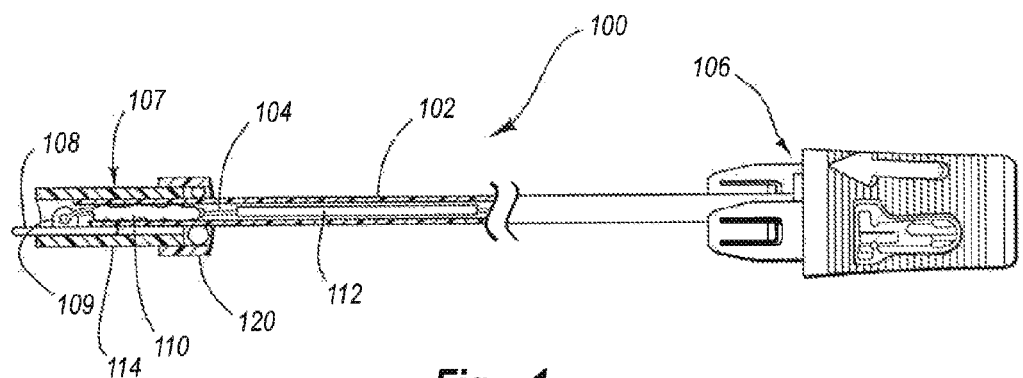
FIG. 1 is a partial cut-away view of a tissue puncture closure device according to the prior art.

As mentioned above, vascular procedures are conducted throughout the world and require access to a vessel through a puncture. Most often, the vessel is a femoral artery. To close the puncture following completion of the procedure, many times a closure device is used to sandwich the puncture between an anchor and a sealing plug. However, sometimes the sealing plug is difficult to eject from the tissue puncture closure device and may not properly seat against an exterior situs of the arteriotomy. If the plug does not seat properly against the arteriotomy, there is a potential for elongated bleeding.

The present disclosure describes methods and apparatus that facilitate sealing plug ejection and proper placement of the sealing plug. One aspect of the present disclosure is directed to the use of a cam structure, such as a suture cam path, in a tissue puncture closure device as part of an automatic or semi-automatic driving assembly. The cam structure may be part of a spool assembly about which a portion of a suture is wound. The cam structure may be defined by a plurality of post members arranged along a contoured (e.g., cam shaped) path. When the suture wraps around the plurality of post members, from one post member to the next post member in series, the suture may extend along a cam shaped suture path. Rotation of the spool assembly unwinds the suture from the post members thereby providing a variable rotational or torsional force.

The spool assembly may be connected to a driving plate or other device that is connected to a compaction member assembly. In some arrangements, the spool assembly is arranged coaxially with the driving plate, wherein rotation of the spool assembly results in rotation of the driving plate about a common axis. The compaction member assembly may include a compaction tube at a distal end thereof that is arranged to contact the sealing plug. The compaction member assembly may also include a coil at a proximal end thereof operable between the compaction tube and the driving plate. The driving plate may include at least one stop structure arranged to contact the coil, and rotation of the driving plate cause the coil to advance the compaction member. Unwinding of the suture from the cam member upon rotation of the spool assembly may result in application of a variable driving force to the proximal end of the compaction assembly upon rotation of the spool assembly.

While the vascular instruments shown and described below includes procedure sheaths and puncture sealing devices, the application of principles described herein are not limited to the specific devices shown. The principles described herein may be used with any medical device. Therefore, while the description below is directed primarily to arterial procedures and certain embodiments of a tissue puncture closure device, the methods and apparatus are only limited by the appended claims.

As used in this specification and the appended claims, the terms "compact," "compaction," and "compacting" are used broadly to mean packing down and compressing by one or a succession of blows or taps or smooth, steady pressure, but not by excessive force. The terms "tamp" and "tamping" may relate to certain types or forms of "compaction" and "compacting." "Engage" and "engagable" are also used broadly to mean interlock, mesh, or contact between two devices. Likewise "disengage" or "disengagable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as used in the specification, including the claims, have the same meaning as the word "comprising."

Referring to FIGS. 1-4, a tissue puncture closure device 100 is shown according to the prior art. Some example closure devices are disclosed in U.S. Published Patent Application No. 2005/0085851 and U.S. Pat. Nos. 7,618,438 and 7,618,436, which references are incorporated herein in their entirety by this reference. The tissue puncture closure device 100 includes a carrier tube 102 with a filament or suture 104 extending at least partially therethrough. The tissue puncture closure device 100 also includes a first or proximal end 106 and a second or distal end 107. External to the distal end 107 of the carrier tube 102 is an anchor 108. The anchor may include an elongated, stiff, low profile member including an eye 109 formed at the middle. The anchor 108 is typically made of a biologically resorbable polymer.

The suture 104 is threaded through the anchor 108 and back to a collagen pad 110. The collagen pad 110 may comprise, for example, randomly oriented fibrous material bound together by chemical means. The collagen pad 110 is slidingly attached to the suture 104 as the suture passes distally through the carrier tube 102. As the suture traverses the anchor 108 and reenters the carrier tube 102, the suture 104 is securely slip knotted proximal to the collagen pad 110 to facilitate cinching of the collagen pad 110 when the tissue puncture closure device 100 is properly placed and the anchor 108 deployed (see FIG. 4).

The carrier tube 102 typically includes a compaction member 112 disposed therein. The compaction member 112 is slidingly mounted on the suture 104 and may be used by an operator to compact the collagen pad 110 toward the anchor 108 at an appropriate time to seal a percutaneous tissue puncture.

Prior to deployment of the anchor 108 within an artery, the eye 109 of the anchor 108 rests outside the distal end 107 of the carrier tube 102. The anchor 108 may be temporarily held in place flush with the carrier tube 102 using a bypass tube 114 that is disposed over the distal end 107 of the carrier tube 102.

Figure 2:
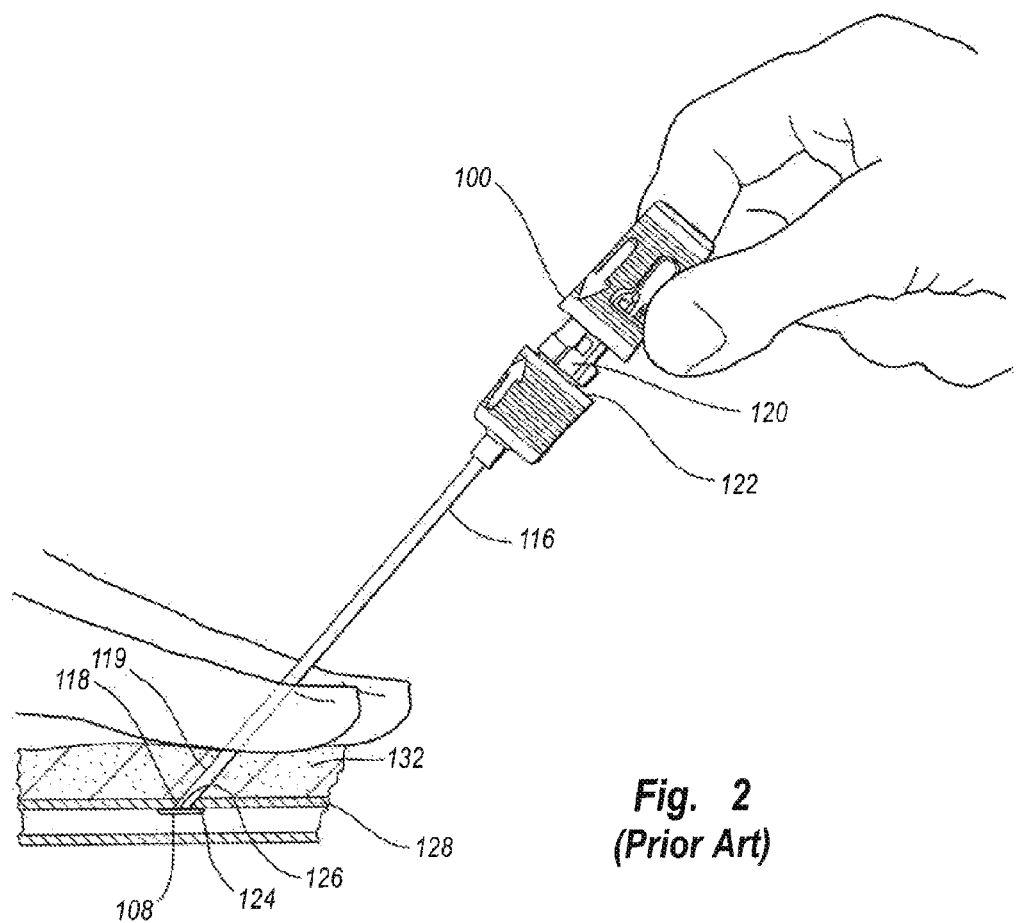
FIG. 2 is a side view of the tissue puncture closure device of FIG. 1 engaged with an artery according to the prior art.
Figure 3:
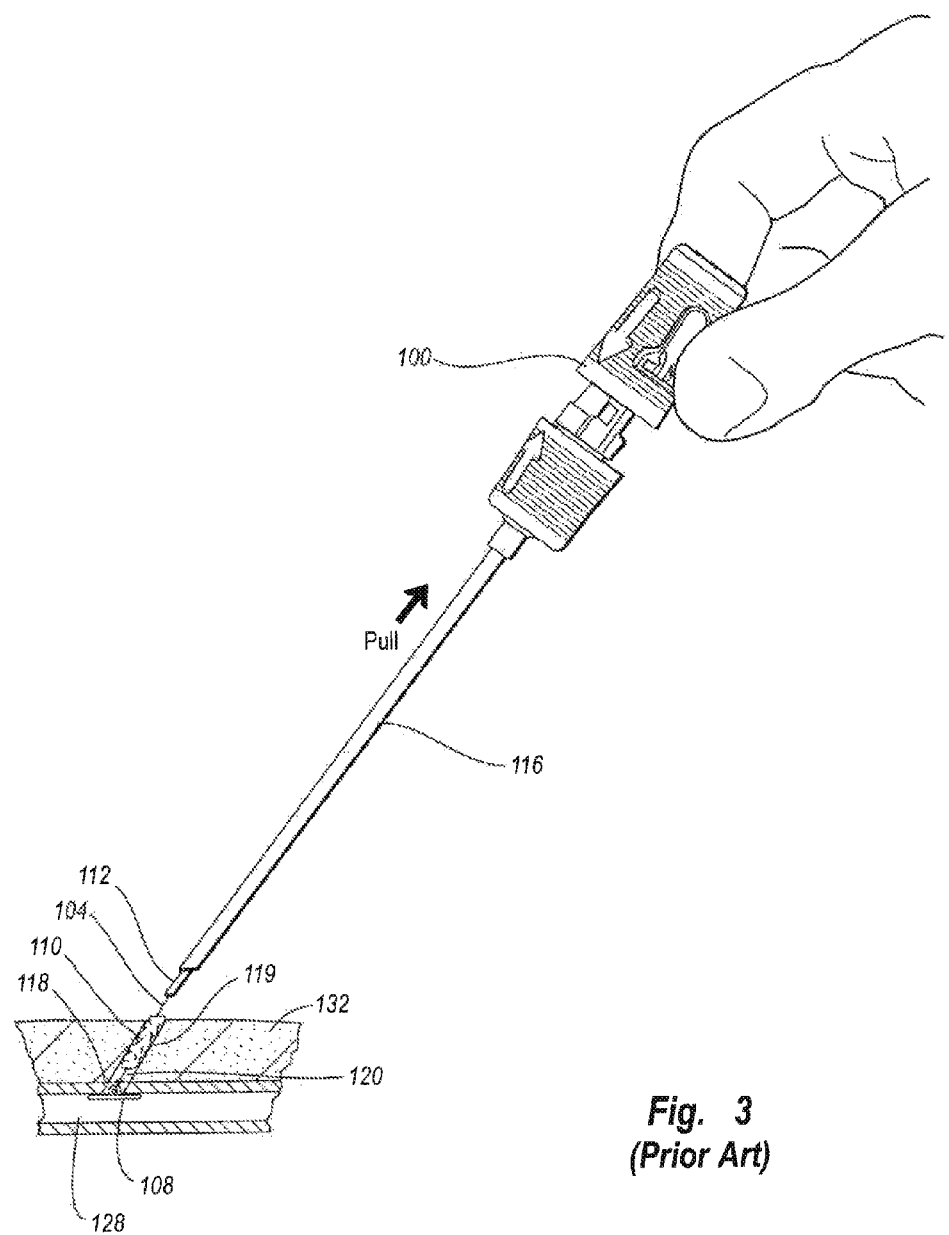
FIG. 3 is a side view of the tissue puncture closure device of FIG. 1 being withdrawn from a vessel according to the prior art to deploy a sealing plug.
Figure 4:
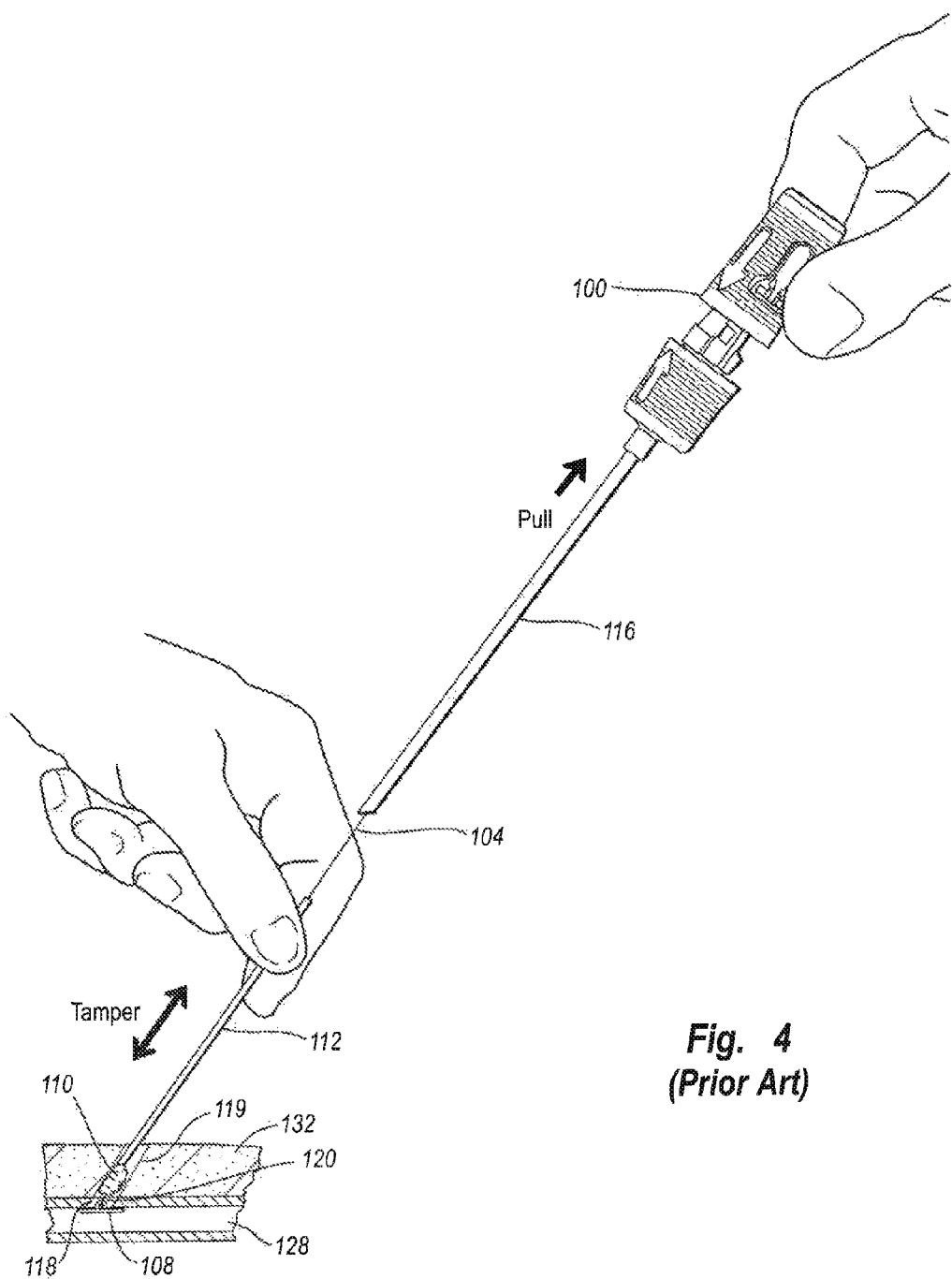
FIG. 4 is a side view of the tissue puncture closure device of FIG. 1 illustrating compaction of the sealing plug according to the prior art.

The flush arrangement of the anchor 108 and carrier tube 102 allows the anchor 108 to be inserted into a sheath such as insertion sheath 116 as shown in FIGS. 2-4, and eventually through a tissue (e.g., arterial) puncture 118. The insertion sheath 116 is shown in FIGS. 2-4 inserted through a percutaneous incision 119 of a tissue layer 132 and into an artery 128. The bypass tube 114 (see FIG. 1) includes an oversized head 120 that prevents the bypass tube 114 from passing through an internal passage of the insertion sheath 116. As the tissue puncture closure device 100 is inserted into the insertion sheath 116, the oversized head 120 bears against a surface 122 of insertion sheath 116.

Further insertion of the tissue puncture closure device 100 results in sliding movement between the carrier tube 102 and the bypass tube 114, thereby releasing the anchor 108 from the bypass tube 114 (see FIG. 1). The anchor 108 typically remains in the flush arrangement shown in FIG. 1 following release from the bypass tube 114, limited in movement by the insertion sheath 116.

The insertion sheath 116 may include a monofold at a second or distal end 126 thereof. The monofold acts as a one-way valve to the anchor 108. A monofold is typically a plastic deformation in a portion of the insertion sheath 116 that elastically flexes as the anchor 108 is pushed out through the distal end 126 of the insertion sheath 116. Typically, after the anchor 108 passes through the distal end 126 of the insertion sheath 116 and enters the artery 128, the anchor 108 is no longer constrained to the flush arrangement with respect to the carrier tube 102 and it deploys and rotates to the position shown in FIG. 2.

The insertion sheath 116 may include a pair of closure device connection apertures (not shown) and a carrier tube aperture (not shown) at a proximal surface 122 (see FIG. 1). The carrier tube 102 is inserted into the carrier tube aperture and the sheath connection members 130 are inserted into and releaseably engage with the closure device connection apertures when assembling the tissue puncture closure device 100 with the insertion sheath 116.

Referring next to FIGS. 3-4, with the anchor 108 deployed, the tissue puncture closure device 100 and the insertion sheath 116 are withdrawn together, ejecting the collagen pad 110 from the carrier tube 102 into the percutaneous incision 119 and exposing the compaction member 112. With the compaction member 112 fully exposed as shown in FIG. 4, the collagen pad 110 is manually compacted, and the anchor 108 and collagen pad 110 are cinched together and held in place with the self-tightening slip-knot on the suture 104. The tissue puncture is sandwiched between the anchor 108 and the collagen pad 110, thereby sealing the tissue puncture 118. The suture 104 is then cut and the percutaneous incision 119 may be closed. The suture 104, anchor 108, and collagen pad 110 are generally made of resorbable materials and therefore remain in place while the tissue puncture 118 heals.

It may be difficult to eject and compact the collagen pad 110 using the typical tissue puncture closure device 100 described above. The insertion sheath 116 resists deformation as the collagen pad 110 is ejected from the carrier tube and compaction does not commence until the insertion sheath 116 has been removed so as to expose the compaction member 112 for manual grasping. Under certain conditions, removal of the insertion sheath 116 prior to compacting the collagen pad 110 causes the collagen pad 110 to retract or displace proximally from the tissue puncture 118, creating an undesirable gap between the collagen pad 110 and the tissue puncture 118.

The general structure and function of tissue puncture closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

Referring now to FIGS. 5-15, an apparatus, for example a tissue puncture closure device 200, is shown according to one embodiment of the present disclosure. The closure device 200 is shown as an assembly in the exploded perspective views of FIGS. 5A-5B. FIGS. 5C-5H illustrate the closure device 200 assembled and inserted through a procedure sheath 216 and into a lumen 232.

The closure device 200 has particular utility when used in connection with intravascular procedures, such as angiographic dye injection, cardiac catheterization, balloon angioplasty and other types of recanalizing of atherosclerotic arteries, etc. as the closure device 200 is designed to cause immediate hemostasis of the blood vessel (e.g., arterial) puncture. However, it will be understood that while the description of the preferred embodiments below are directed to the sealing off of percutaneous punctures in arteries, such devices have much more wide-spread applications and can be used for sealing punctures or incisions in other types of tissue walls as well. Thus, the sealing of a percutaneous puncture in an artery, shown herein, is merely illustrative of one particular use of the closure device 200 according to principles of the present disclosure.

The closure device 200 includes a first or proximal end portion 206 and a second or distal end portion 207. A carrier tube 202 extends from the proximal end portion 206 to the distal end portion 207 and includes an outlet 213 at the distal end portion 207. The distal end portion 207 may include a slit 209.

The carrier tube 202 may be made of plastic or other material and is designed for insertion through the procedure sheath 216. The procedure sheath 216 is designed for insertion through a percutaneous incision 219 in a tissue layer 230 and into the lumen 232. According to FIGS. 5C-5H, the lumen 232 comprises an interior portion of a femoral artery 228.

At the distal end portion 207 of the carrier tube 202 there is an anchor 208 and a sealing plug 210. The anchor 208 of the present embodiment is an elongated, stiff, low-profile member arranged to be seated inside the artery 228 against an artery wall 234 contiguous with a tissue puncture 218. The anchor 208 is preferably made of a biologically resorbable polymer. The sealing plug 210 is formed of a compressible sponge, foam, or fibrous mat made of a non-hemostatic biologically resorbable material such as collagen, and may be configured in any shape so as to facilitate sealing the tissue puncture 218.

Figure 5A:
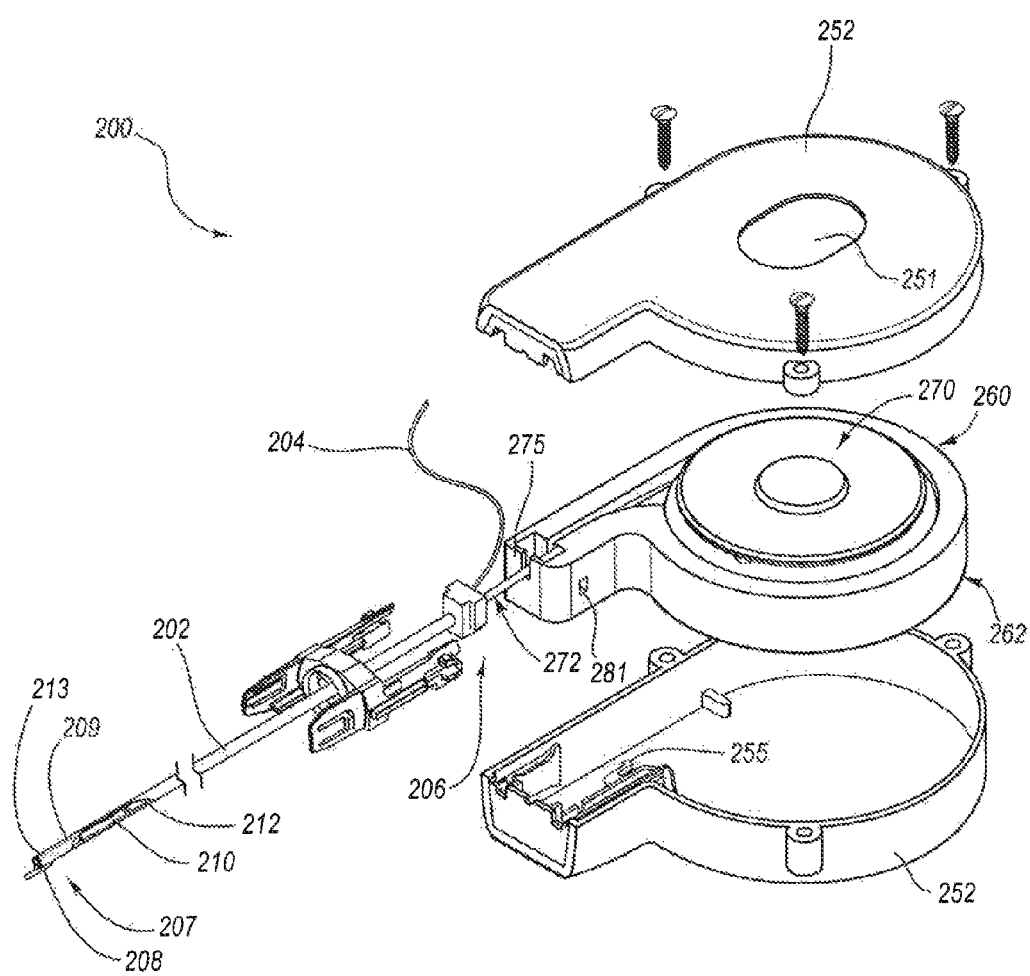
FIG. 5A is an exploded perspective view of an example tissue puncture closure device with an automatic compaction mechanism having a disengagable cam system according to the present disclosure.
Figure 5B:
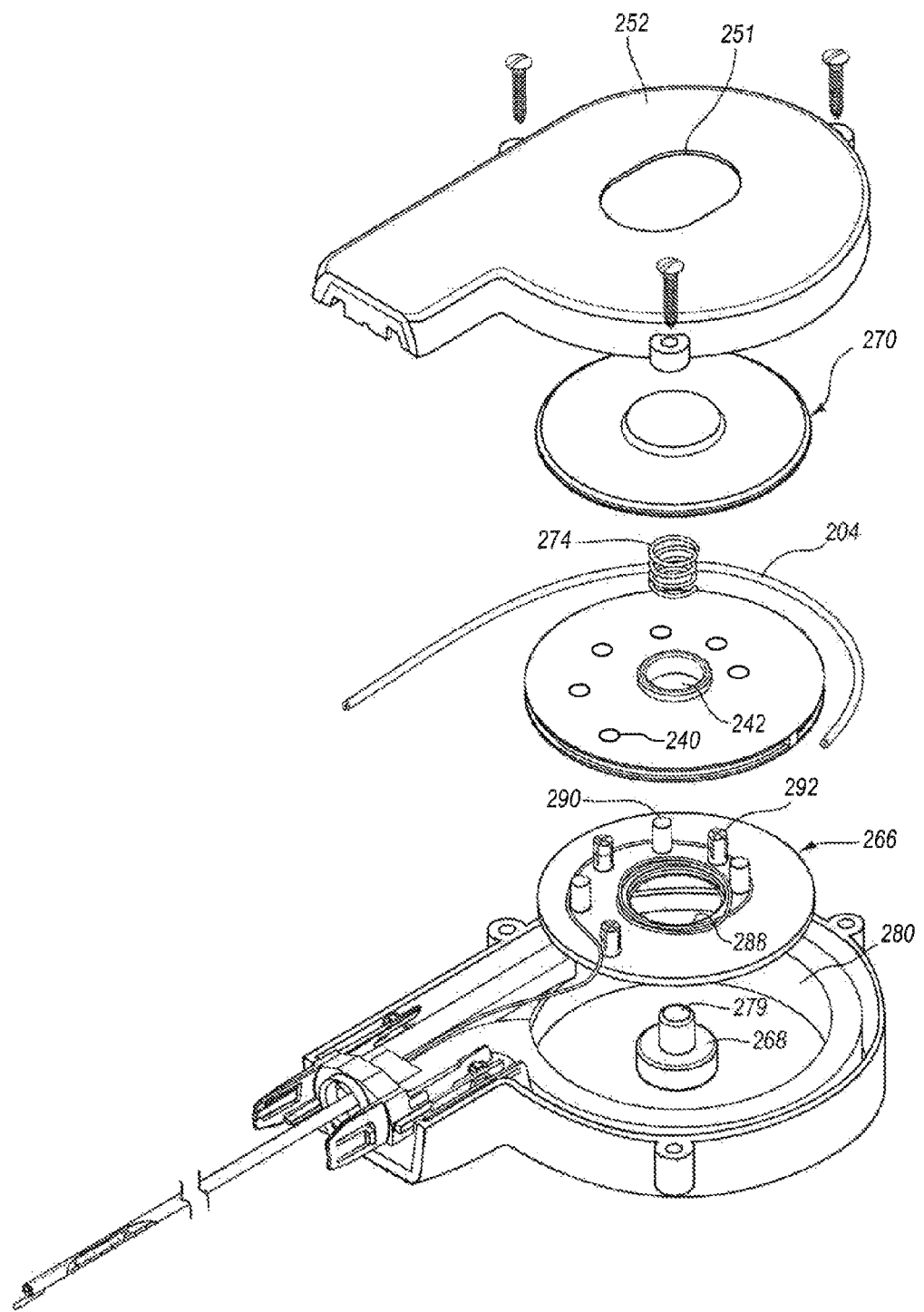
FIG. 5B is another exploded perspective view of the tissue puncture closure device of FIG. 5A.

The sealing plug 210 and anchor 208 are connected to one another by a connector such as a filament or suture 204 that is also biologically resorbable. The anchor 208, the sealing plug 210, and the suture 204 may be collectively referred to as the "closure elements" below. As shown in FIGS. 5A-5B, the anchor 208 is initially arranged adjacent to and exterior of the distal end portion 207 of the carrier tube 202, while the sealing plug 210 is initially disposed within the carrier tube 202. The anchor 208 is shown nested in its low profile configuration along the carrier tube 202 to facilitate insertion into the lumen 232 in FIGS. 5A-5B, and deployed abutting the artery wall 234 in FIGS. 5C-5H.

The suture 204 extends distally from the proximal end portion 206 of the closure device 200 through the carrier tube 202. The suture 204 may be threaded through one or more perforations in the sealing plug 210, through a hole in the anchor 208, and proximally back toward the carrier tube 202 to the sealing plug 210. The suture 204 is preferably threaded again through a perforation or series of perforations in the sealing plug 210. The suture 204 may also be threaded around itself to form a self-tightening slip-knot. The suture 204 may thus connect the anchor 208 and the sealing plug 210 in a pulley-like arrangement to cinch the anchor 208 and the sealing plug 210 together when the carrier tube 202 is pulled away from the anchor 208 and the sealing plug 210. The anchor 208 and the sealing plug 210 sandwich and lock the anchor and plug together, sealing the tissue puncture 218.

The carrier tube 202 may house a compaction device or compaction member, such as a compaction tube 212, for advancing the sealing plug 210 along the suture 204 and toward the anchor 208. The compaction tube 212 is shown located partially within the carrier tube 202 and proximal of the sealing plug 210. The compaction tube 212, however, also extends through a handle or housing 252 of the closure device 200. The compaction tube 212 is preferably an elongated tubular or semi-tubular member that may be rigid or flexible and formed of any suitable material. For example, according to one embodiment, the compaction tube 212 is made of polyurethane. The suture 204 extends through at least a portion of the compaction tube 212. For example, as shown in FIGS. 5A-5H, the suture 204 extends along the compaction tube 212 between the proximal and distal end portions 206, 207. However, the suture 204 is not directly connected to the compaction tube 212. Accordingly, the suture 204 and the compaction tube 212 may slide past one another.

According to the embodiment of FIGS. 5A-5H, the suture 204 attaches to an automatic driving assembly 260 (see also FIGS. 6-15). The automatic driving assembly 260 may include a base 262, a driving plate 264, a spool assembly 266, a bearing 268, a release member 270, a coil 272, and a biasing member 274. The automatic driving assembly 260 may, in some arrangements, also include the compaction tube 212 and carrier tube 202. In other arrangements, features of the automatic driving assembly 260, such as the coil 272, may be eliminated or provided as a separate feature of the closure device 200.

Figures 5E, 5F:
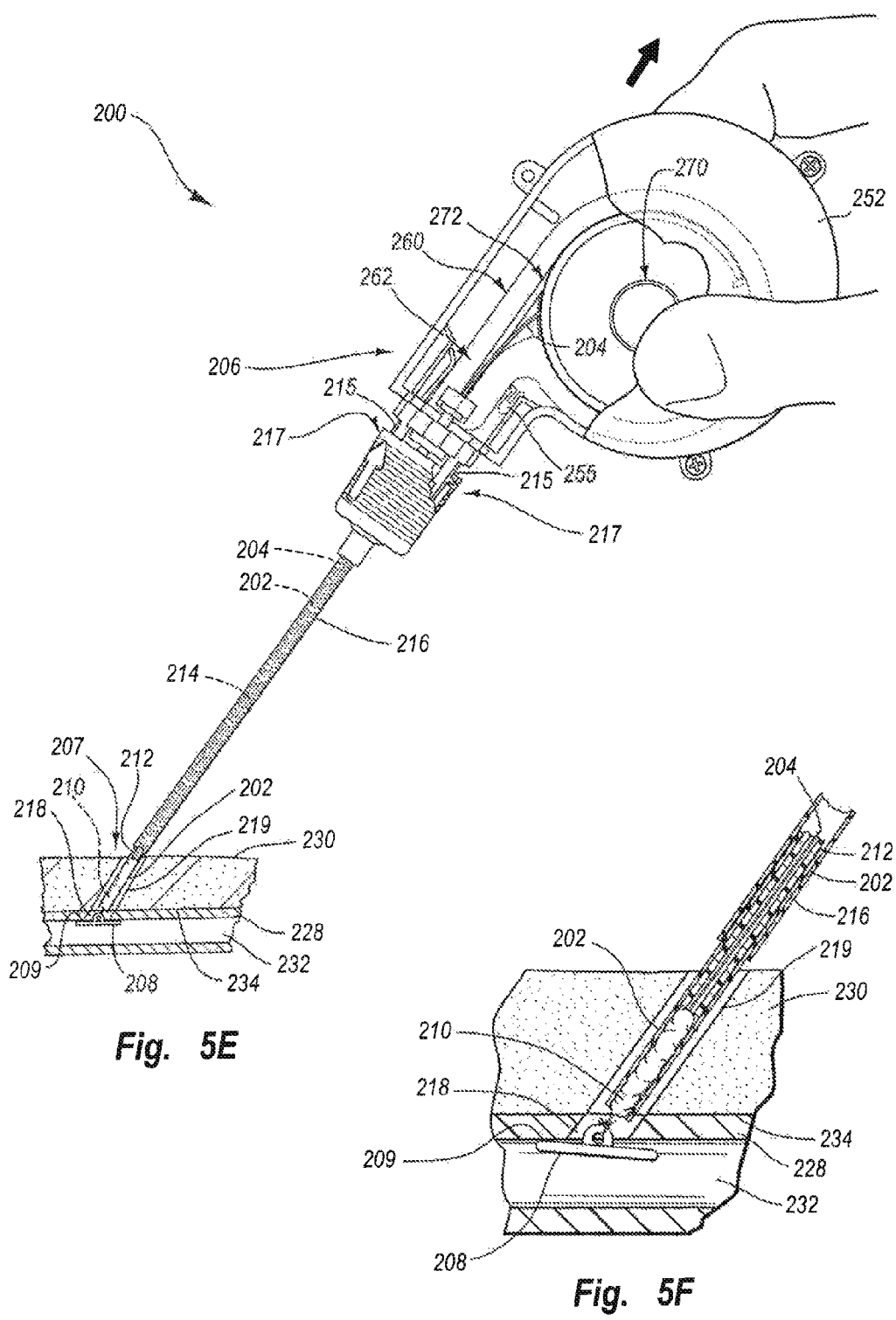
FIG. 5E is a side view of the tissue puncture closure device of FIG. 5A shown engaged with a vessel in a second position with the procedure sheath retracted.
FIG. 5F is a detailed inset of FIG. 5E.

The base 262 may include a distal end 275, a connector recess 276, a coil recess 278, a spool recess 280, a detent recess 281, and an axle 279. The base 262 is movable within the housing 252. As shown in FIG. 5E, the base 262 may slide forward in the housing 252 until the distal end 275 contacts an internal surface of the housing 252.

The connector recess 276 may be sized to receive a connector feature used to secure the carrier tube 202 to the automatic driving assembly. The coil recess 278 may be sized to receive a portion of the coil 272. The spool recess 280 may be sized to receive the driving plate 264, spool assembly 266, release member 270 and other features of the automatic driving assembly 260. The detent recess 281 may be sized and arranged to receive a portion of a stowage detent 255 that assists in temporarily holding the base 262 in a retracted position in the housing 252. Further details concerning operation of the stowage detent 255 are included below. The axle 279 may be arranged to support the bearing 268 by extending through a bearing opening 282, and orient the driving plate 264 and spool assembly 266 within the spool recess 280.

Figure 13:
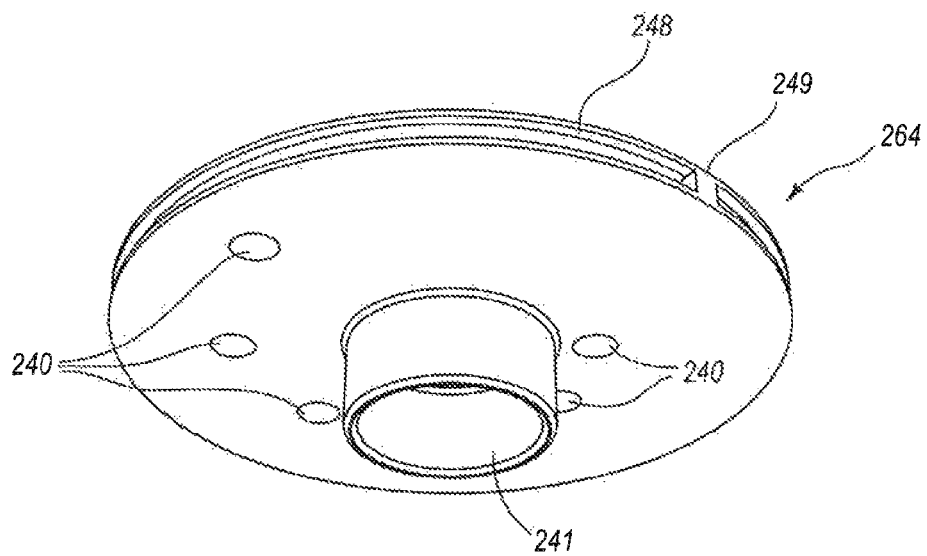
FIG. 13 is a bottom perspective view of a driving plate of the compaction assembly of FIG. 6.

The driving plate 264 may include a plurality of post apertures 240, a bearing aperture 241, a hub aperture 242, a bearing hub 243, a top surface 244, a bottom surface 246, a coil track 248, and a coil stop 249 (see FIGS. 5B and 13). The post apertures 240 may be sized to receive suture posts of the spool assembly 266 (e.g., posts 290, 292 described below). The post apertures 240 may have different shapes and be sized to receive suture posts of varying shapes and sizes. In some arrangements, the post apertures 240 may be sized and constructed to provide a snap-fit or interference connection between at least some of the post members and the driving plate 264.

The bearing aperture 241 is sized to receive at least a portion of the bearing 268. In some arrangements, the bearing 268 is secured to the driving plate 264 within the bearing aperture 241 using, for example, a press-fit connection. The bearing hub 243 may define the bearing aperture 241. The bearing hub 243 may provide a structure that aligns the spool assembly 266 with the driving plate 264.

The coil track 248 may be sized to receive a portion of the coil 272. The coil track 248 may be defined around a periphery of the driving plate 264. In one arrangement, the coil track 248 extends around an entire periphery of the driving plate 264. In other arrangements, the coil track 248 may be defined by other portions of the driving plate 264 such as, for example as a recess in the top or bottom surface 244, 246 of the driving plate 264, or a recess or track defined in a surface of the base 262, spool assembly 266, or release member 270.

The coil stop 249 may be positioned in the coil track 248. The coil stop 249 may define a contact surface against which a portion of the compaction tube assembly (e.g., a proximal end of the coil 272) contacts to transfer rotational forces from the driving plate 264 to longitudinal movement of the compaction tube assembly. Typically, rotation of the driving plate 264 advances the compaction tube assembly by applying a force to a proximal end of the compaction tube assembly (e.g., a proximal end of the coil 272 or the compaction tube 212). In other arrangements, other features of the driving plate 264, such as a compression fit between the coil 272 and coil track 248, may be used to transfer the rotational forces of the driving plate 264 to advance the compaction tube assembly.

Figure 10:
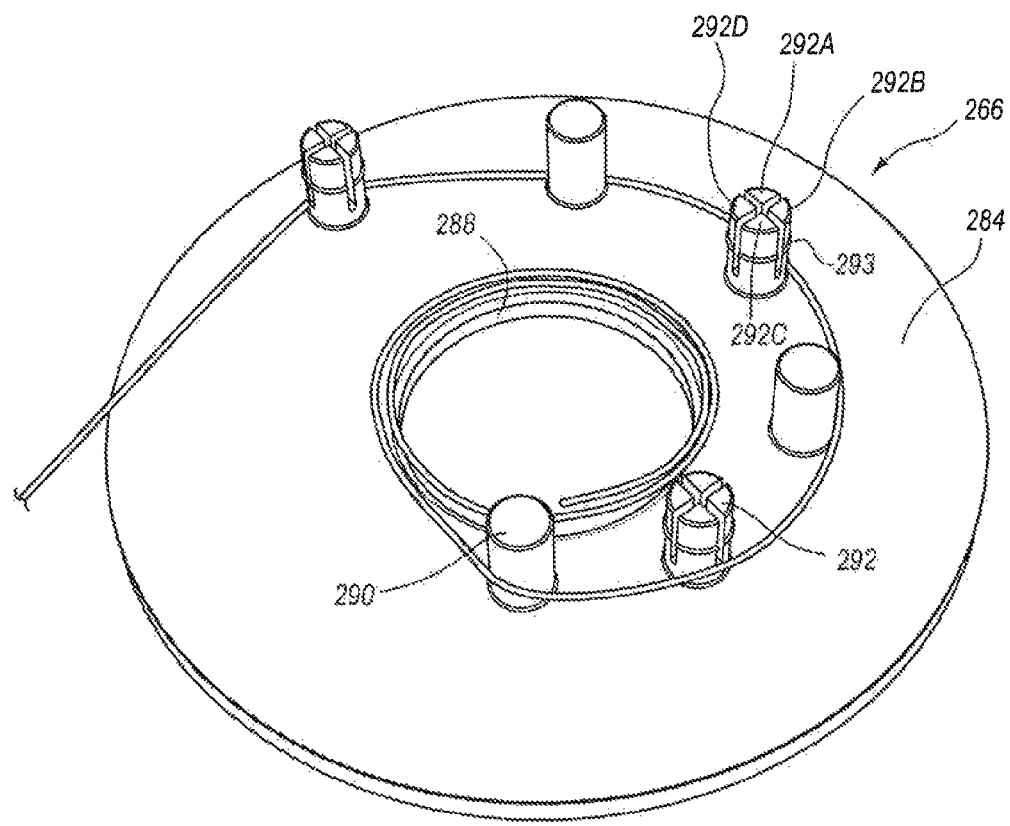
FIG. 10 is a top perspective view of a spool assembly of the compaction assembly of FIG. 6.
Figure 11:
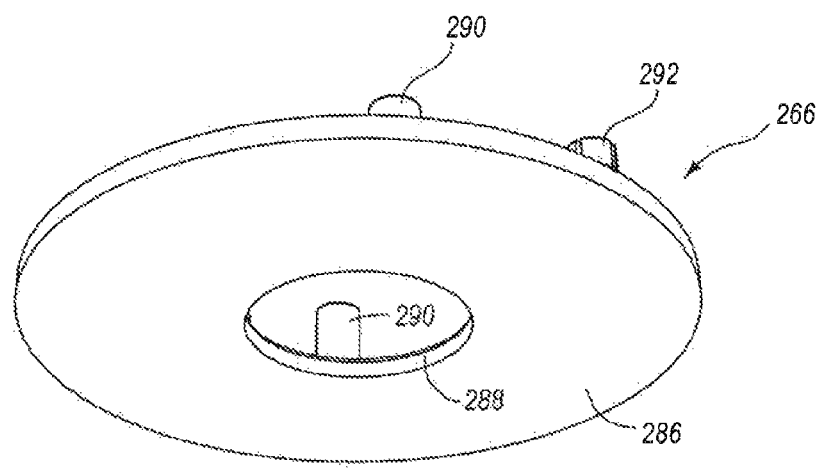
FIG. 11 is a bottom perspective view of the spool assembly of FIG. 10.
Figure 12:
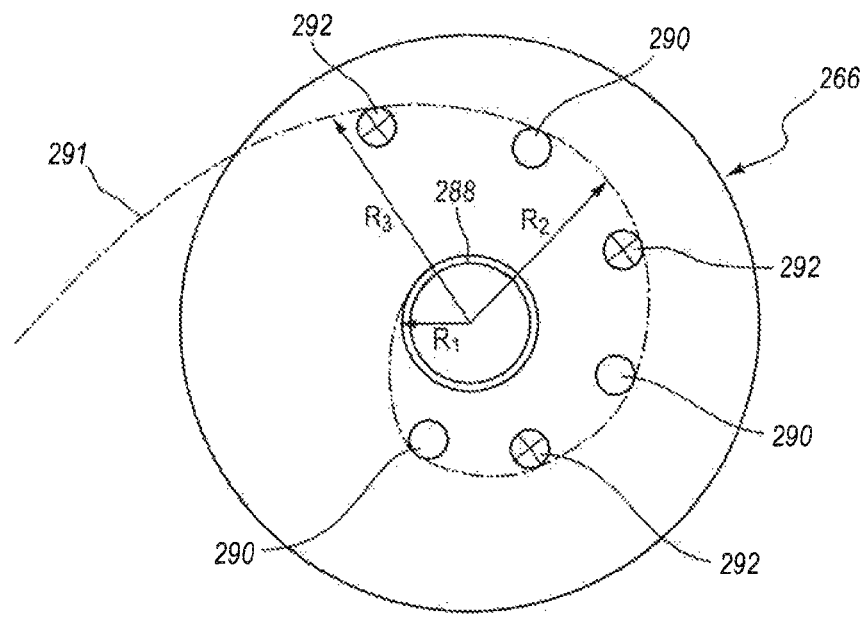
FIG. 12 is a top view of the spool assembly of FIG. 10.

The spool assembly 266 may include a top surface 284, a bottom surface 286, an aperture 288, at least one solid post 290, and at least one connector post 292 (see FIGS. 10-12). The solid and connector posts 290, 292 may extend from the top surface 284. In some arrangements, the solid and connector posts 290, 292 may be integrally formed with the top surface 284. In other arrangements, the solid and connector posts 290, 292 may extend from the bottom surface 286, through the spool assembly 266, and protrude from the top surface 284.

The aperture 288 may be sized to extend over the bearing hub 243 of the driving plate 264. In some arrangements, the spool assembly 266 may be connected to the driving plate 264 by an interface between the aperture 288 and the bearing hub 243. In other arrangements, at least some of the solid posts 290 and connector posts 292 may provide a connection between the driving plate 264 and spool assembly 266.

The number and type of posts used with the spool assembly 266 may vary. Typically, at least 2 to 3 posts are needed to provide a suture path about which the suture 204 is wound. The number of posts may range in some embodiments from 2 to 20 posts, and more preferably about 5 to 10 posts to define the suture path within the spool assembly.

The solid and connector posts 290, 292 may be arranged on the spool assembly 266 in a pattern that provides a cam shaped suture path 291 (see FIG. 12). The suture path 291 may have a variable radius that changes from $R_1$ near the aperture 288, to $R_2$ and $R_3$ moving along the arrangement of posts toward an exit for the suture 204 from the spool assembly 266. The suture path 291 may be defined as a variable radius suture path. The suture 204 may wrap at least one complete wrap around any one of the solid and connector posts 290, 292 to anchor the suture 204. In some arrangements, the suture 204 is anchored about another portion of the spool assembly 266 such as the hub 296 of the release member 270.

The solid posts 290 may have a generally solid, continuous construction. The solid posts 290 may be sized smaller than the post apertures 240 of the driving plate 264 to permit unrestricted axial movement of the solid posts 290 relative to the driving plate 264.

The connector posts 292 may be constructed to provide some amount of connection between the driving plate 264 and spool assembly 266. In one example, the connector posts 292 include at least one flexible arm, tab, lip, or other structure that creates at least a temporary connection between the driving plate 264 and spool assembly 266 upon insertion of the connection post 292 through one of the post apertures 240. The connector posts 292 shown in at least FIG. 10 are each divided into four arms 292A-D. Each of the arms 292A-D may be flexible and able to move to permit insertion of the connector post 292 into the post aperture 240 and to resist removal of the connector post 292 from the post aperture 240. A lip or protrusion 293 may extend around at least a portion of the connector posts 292 to provide further connection between the connector posts 292 and the driving plate 264. The operation of the connector posts 292 may provide some tactile feel for the operator as connector posts 292 move axially relative to the driving plate 264.

The connector posts 292 may have a size (e.g., diameter) in a rest state that is the same or greater than a size (e.g., diameter) of the post apertures 240. In some arrangements, the connector posts 292 have a smaller size than the post apertures 240 to provide unrestricted axial movement between the driving plate 264 and spool assembly 266.

Figure 14:
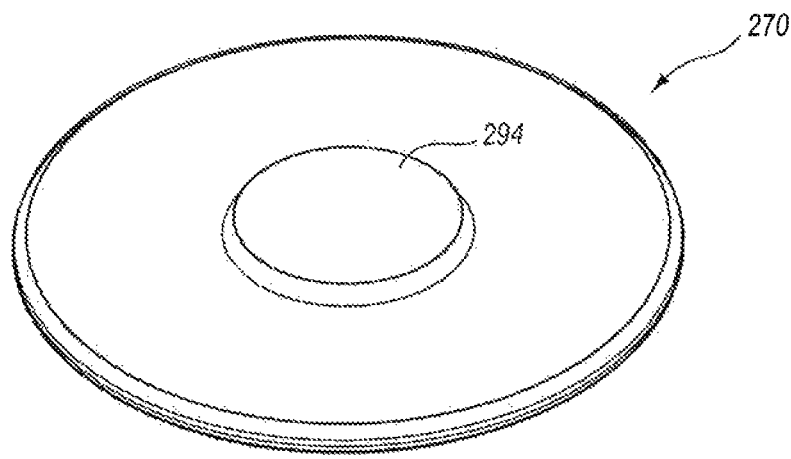
FIG. 14 is a top perspective view of a release member of the compaction assembly of FIG. 6.
Figure 15:
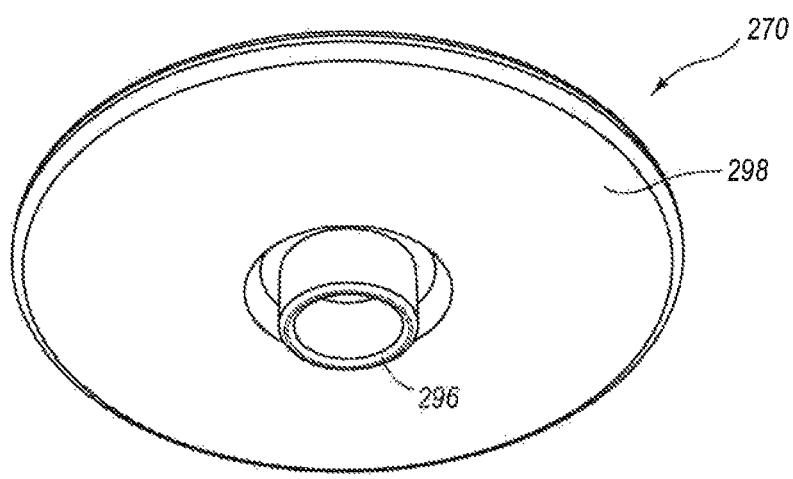
FIG. 15 is a bottom perspective view of the release member of FIG. 14.

The release member 270 may include an actuator portion 294, a hub 296, and a post contact surface 298 (see FIGS. 14-15). The actuator portion 294 may extend through a release member opening or slot 251 of the housing 252 to be accessible by an operator of the closure device 200 outside of the housing 252. The release member opening 251 may be sized to permit some longitudinal (i.e., toward anchor 208) movement of the release member 270 relative to the housing 252.

The hub 296 may be sized and arranged to extend through the hub aperture 242 of the driving plate. The hub 296 may define a recess that is sized to receive a portion of the biasing member 274. An outer surface of the hub 296 may be configured to have a portion of a proximal end of the suture 204 wound thereon to provide an anchor for the suture 204. The post contact surface 298 may be arranged to contact and move at least one of the solid and connector posts 290, 292 relative to the driving plate 264 upon application of a compressive force to the actuator portion 294 (see FIGS. 7-8). The biasing member 274 may operate to move the release member 270 from the compressed position shown in FIG. 9 to the rest position shown in FIG. 8.

Figure 6:
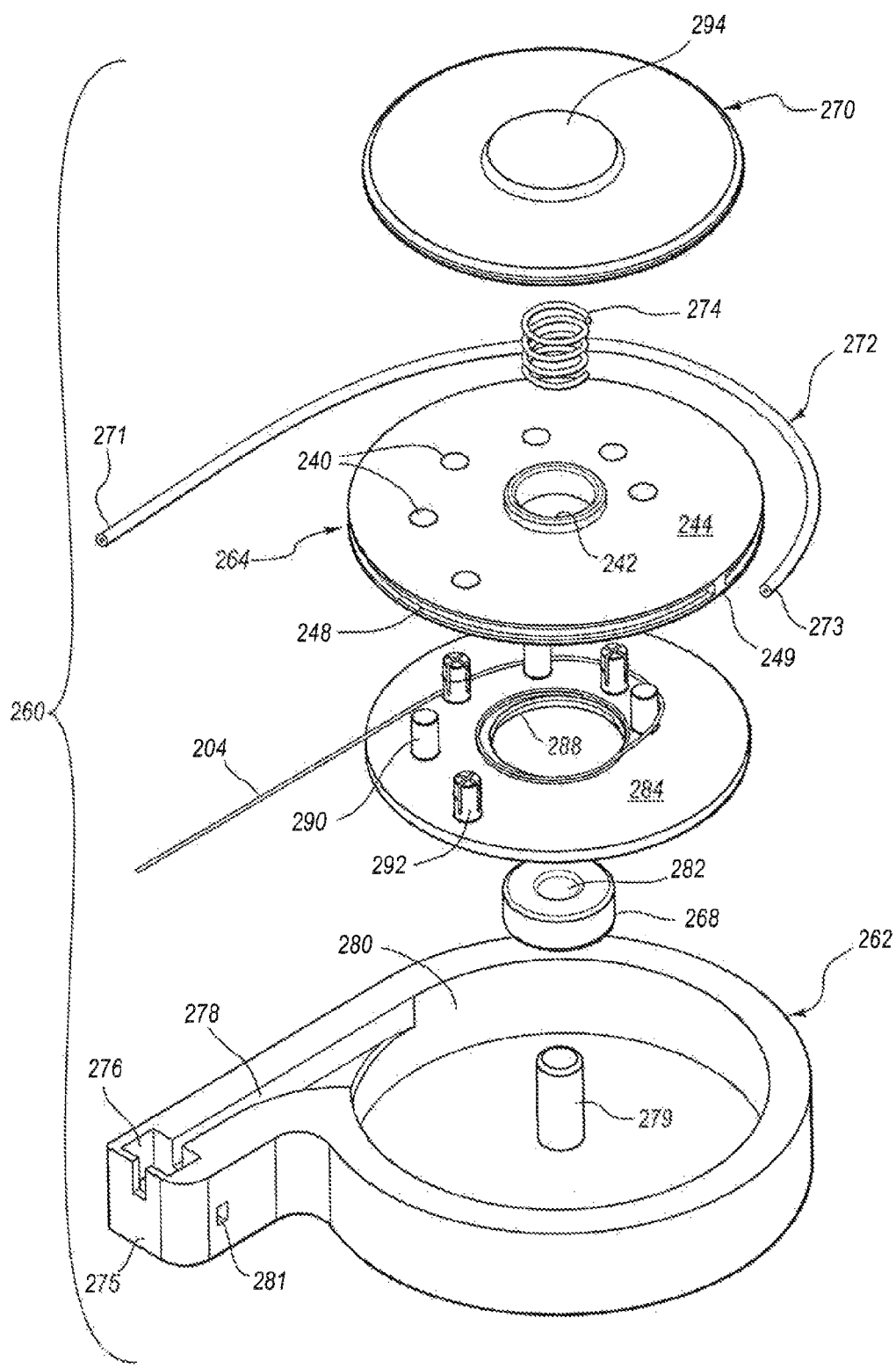
FIG. 6 is an exploded perspective view of a compaction assembly of the tissue puncture closure device of FIG. 5A.

The coil 272 includes a distal end 271 and a proximal end 273 (see FIG. 6). The distal end 271 may abut the compaction tube 212 (e.g., at a proximal end of the compaction tube 212). The proximal end 273 may abut the coil stop 249 of the driving plate 264. The cam construction of the cam shaped suture path 291 that the suture 204 follows as the spool assembly 266 rotates to provide a variable linear force to the coil 272 through the driving plate 264 that advances the compaction tube 212 toward the sealing plug 210.

In some arrangements, the automatic driving assembly 260 may include the compaction tube 212. The compaction tube 212 and coil 272 may together define a compaction tube assembly. The compaction tube assembly may be positioned proximal of and adjacent to the sealing plug 210. The entire automatic driving assembly 260, including the compaction tube 212, may move together longitudinally within the housing 252 as shown by comparison of FIGS. 5C and 5E.

The automatic driving assembly 260 is located within the housing 252 at the proximal end portion 206 of the closure device 200. Embodiments of the automatic driving assembly 260 may be selectively disengagable. For example, operation of the release member 270, which protrudes through the release member opening 251 in the housing 252, may release the spool assembly 266 to permit unspooling of the suture 204. Operating the release member 270 may release at least some length of the suture 204 from the housing 252. Unspooling or release of some length of the suture 204 after compaction of the sealing plug 210 permits the operator withdraw the tissue puncture closure device 200 without further compacting the sealing plug 210. With the tissue puncture closure device 200 further withdrawn from the percutaneous incision 219, the operator is more easily able to cut the suture 204 at a location proximal of the sealing plug 210.

Figure 7:
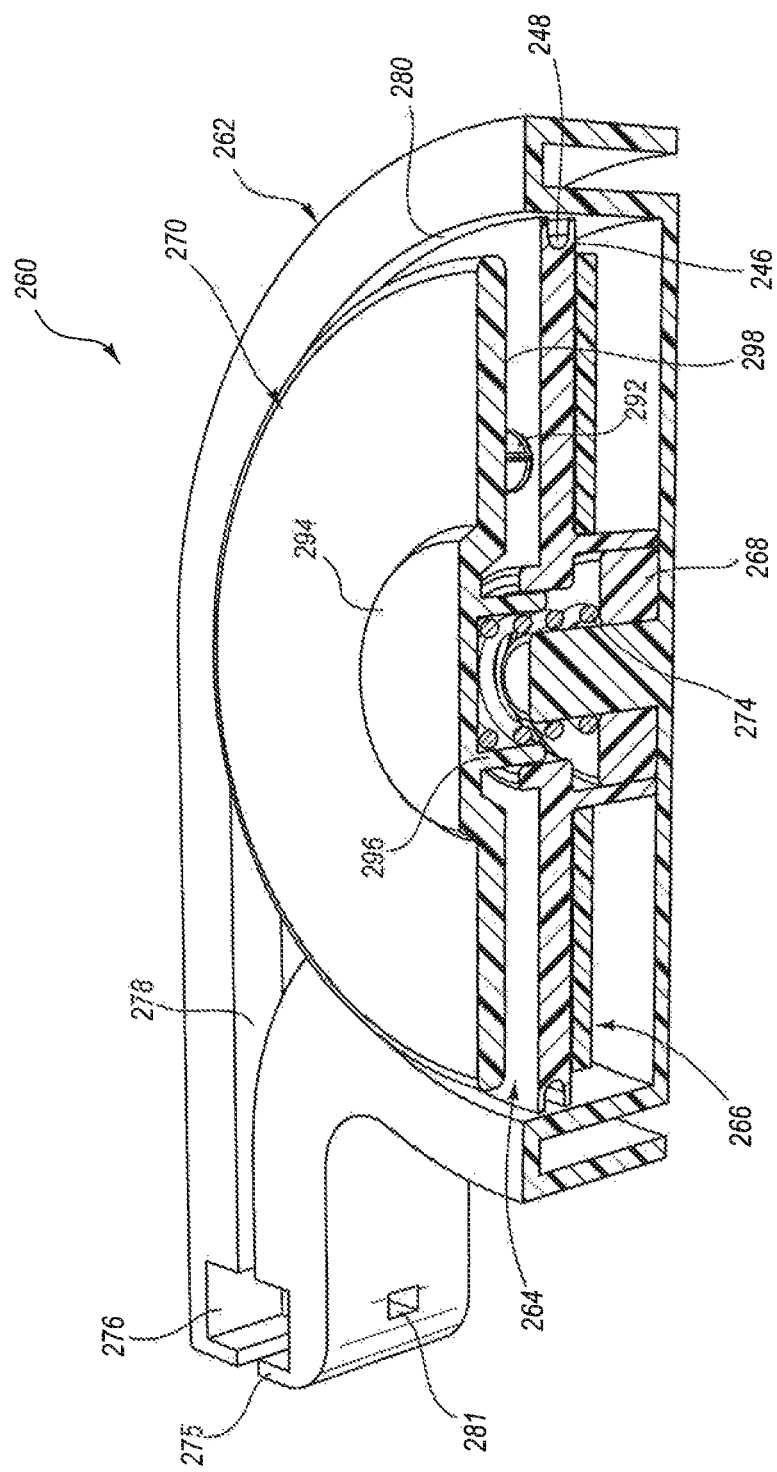
FIG. 7 is a perspective cross-sectional view of the compaction assembly of FIG. 6.

As shown in FIGS. 7-9, the driving plate 264 may be connected to the spool assembly 266. The suture 204 is connected to and at least partially wound about the spool assembly 266. The driving plate 264 tends to rotate at the same angular rate as the spool assembly 266 as a result of the connection between the driving plate 264 and spool assembly 266 with the solid and connector posts 290, 292.

Withdrawal of the closure device 200 from the tissue puncture 218 (if the anchor 208 is deployed and the automatic driving assembly 260 has contacted the stop (see FIGS. 5E and 5G)) causes the suture 204 to unwind from the spool assembly 266. The spool assembly 266 rotates as the suture 204 unwinds and provides a torsional motive force that is transduced to a linear compaction force.

The torsional motive force provided by the spool assembly 266 is transduced into the linear compaction force by the driving plate 264, coil 272 and compaction tube 212. The driving plate 264 may be arranged coaxially with the spool assembly 266. When the spool assembly 266 rotates, it drives the driving plate 264, which in turn drives the coil 272. The coil 272 drives the compaction tube 212, which in turn compacts the sealing plug 210.

The compaction tube 212 is preferably tubular or semi-tubular and partially disposed about the suture 204 along its longitudinal axis. In some arrangements wherein the coil 272 also comprises the compaction tube 212, the coil 272 may comprise a semi-tubular shape having a generally U-shaped cross section, to provide a trough through which the suture 204 may enter and exit laterally. An open trough construction may permit the suture 204 and the coil 272 to merge as the spool assembly 266 unwinds. Accordingly, with the anchor 208 deployed, as the closure device 200 is retracted in a first, proximal direction, the suture 204 unwinds from the spool assembly 266, which drives the driving plate 264. The driving plate 264 drives the coil 272, and the coil 272 drives the compaction tube 212 in a second, opposite or distal direction. The compaction tube 212 compacts the sealing plug 210 toward the anchor 208.

In practice, the carrier tube 202 of the closure device 200 (containing the closure elements described above) is inserted into the procedure sheath 216, which is already inserted within the artery 228 (see FIGS. 5C-5D). As the closure device 200 and the associated closure elements are inserted into the procedure sheath 216, the anchor 208 passes through and out of the distal end of the procedure sheath 216 and is inserted into the lumen 232. As mentioned above and shown in FIGS. 5A-5B, the anchor 208 is initially arranged substantially flush with the carrier tube 202 to facilitate insertion of the anchor 208 through the percutaneous incision 219 and into the lumen 232.

After the anchor 208 passes out of the distal end of the procedure sheath 216, the anchor 208 tends to deploy or rotate to the position shown in FIGS. 5C-5D. The closure device 200 may be partially withdrawn from the procedure sheath 216, catching the anchor 208 on the distal end of the procedure sheath 216 and rotating the anchor 208 to the position shown in FIGS. 5C-5D. The closure device 200 preferably includes a pair of biased fingers 215 that are lockingly received by a matching pair of recesses 217 in the procedure sheath 216. The locking arrangement between the biased fingers 215 and matching recesses 217 may fix the position of the housing 252 relative to the procedure sheath 216.

Following deployment of the anchor 208, the housing 252 and the procedure sheath 216 are withdrawn together. Withdrawing the housing 252 causes the anchor 208 to anchor itself within the artery 228 against the artery wall 234 as shown in FIGS. 5C-5D. Further withdrawing the housing 252 causes the automatic driving assembly 260 to slide forward in the housing 252 as shown in FIG. 5E-5F. Functionally, the anchor 208, sealing plug 210, carrier tube 202, procedure sheath 216, and automatic driving assembly 260 maintain the same axial position upon this further withdrawal of the housing 252, and the procedure sheath 216 and housing 252 move proximally (see FIGS. 5E-5F).

Referring to FIGS. 5E-5F, the distal end portion 207 of the carrier tube 202 is exposed within the percutaneous incision 219 as the housing 252 and the procedure sheath 216 are retracted. The carrier tube 202 may retain its position relative to the tissue puncture 218 until the housing 252 and the procedure sheath 216 have been retracted a predetermined distance. Relative movement between the housing 252/procedure sheath 216 and the carrier tube 202 may be facilitated by a sliding mount arrangement between the automatic driving assembly 260 and the housing 252. However, according to some embodiments the automatic driving assembly 260 is fixed to the housing 252.

As shown by the combination of FIGS. 5C-5H, the automatic driving assembly 260, which is attached to the carrier tube 202, may be free floating or displaceable and slides relative to the housing 252 as the housing 252 and the procedure sheath 216 are retracted. However, the automatic driving assembly 260 may be initially held in a first position relative to the housing 252, as shown in FIG. 5C. For example, as shown in FIG. 5C, the closure device 200 may comprise a temporary holder such as a stowage detent 255 that releasably contacts the automatic driving assembly 260. The stowage detent 255 may be mounted to the housing 252. The stowage detent 255 may include a finger 257 with a protrusion to at least temporarily hold the automatic driving assembly 260 in the first position shown in FIG. 5C by insertion into the detent recess 281 of the base 262. Positioning of the finger 257 in the detent recess 281 may limit premature sliding within the housing 252. In other arrangements, the stowage detent 255 may be mounted to the automatic driving assembly 260 and be releasably connected to the housing 252, such as to a webbing member of the housing 252. In still further arrangements, the stowage detent 255 may be positioned on a back side of the base 262 and interface with features positioned within the housing 252. One or more track members and mating grooves may be used on the base 262 and housing 252 to help maintain alignment of the automatic driving assembly 260 relative to the housing 252 during relative movement there between.

Although the finger 257 tends to hold or temporarily lock the automatic driving assembly 260 in the first position shown in FIG. 5C, the finger 257 releases when a sufficient predetermined force is applied between the housing 252 and the automatic driving assembly 260. For example, with the anchor 208 deployed, a retraction force provided by a user to the housing 252 causes the finger 257 to deflect inward and release. Thereafter, the finger 257 provides little resistance to sliding movement between the automatic driving assembly 260 and the housing 252. Accordingly, retraction of the housing 252 may retract the procedure sheath 216, which is fixedly connected to the housing 252, but the automatic driving assembly 260 and the carrier tube 202 may slide relative to the housing 252 and therefore remain in position with respect to the tissue puncture 218 (see FIG. 5E). The automatic driving assembly 260 may slide a predetermined distance with respect to the housing 252 until the automatic driving assembly 260 reaches a stop (e.g., a distal internal wall of the housing 252). The predetermined distance may be at least long enough to expose the slit 209 (see FIG. 5A) in the carrier tube 202 to facilitate later removal of the sealing plug 210 from the carrier tube 202.

When the automatic driving assembly 260 reaches the stop, further retraction of the housing 252 withdraws the carrier tube 202 as well, ejecting the sealing plug 210 automatically, as shown in FIGS. 5G-5H. The spool assembly 266 begins to rotate to permit unwinding of some of the suture 204 from the spool. Typically, the driving plate 264, which rotates with the spool assembly 266, unwinds an amount to advance the coil 272 and compaction tube 212 and compact the sealing plug 210. Still further retraction of the housing 252 further rotates the spool assembly 266 and driving plate 264 to advance the coil 272 and compaction tube to complete compaction of the sealing plug 210 (see FIGS. 5G-5H). Upon completion of compacting the sealing plug 210, the operator may actuate the release member 270 to disconnect the suture 204 from the solid and connector posts 290, 292 to permit unwinding of the suture 204 from the spool assembly 266. The suture 204 may then be better exposed for cutting near the tissue layer 230 to release the housing 252 from the anchor 208/sealing plug 210.

Unlike previous closure devices that require a separate, manual compaction procedure following the deposition of the sealing plug 210, the closure device 200 of the present disclosure automatically compacts the sealing plug 210 by merely applying a retracting force to the housing 252. The sealing plug 210 may be compacted during or after withdrawal of the carrier tube 202, reducing or eliminating any gaps that may otherwise occur between the sealing plug 210 and the tissue puncture 218 in the artery 228.

In addition, by placing tension on or pulling the suture 204 away from the percutaneous incision 219, the suture 204 may cinch and lock (with a slip knot or the like) together the anchor 208 and the sealing plug 210, sandwiching the artery wall 234 between the anchor 208 and sealing plug 210. The force exerted by the compaction tube 212 and the cinching together of the anchor 208 and sealing plug 210 by the suture 204 also causes the sealing plug 210 to deform radially outward within the percutaneous incision 219 and function as an anchor on the proximal side of the tissue puncture 218 as shown in FIGS. 5G-5H.

Many variations are possible for the features of closure device 200. In some arrangements, the coil 272 may be permanently connected to the driving plate 264. The driving plate 264 may be directly connected to the compaction tube 212. Generally, any device or construction that uses a disengagable cam structure driven by rotation of a spool member (about which the suture is wound) to advance a compaction member to compact a sealing plug falls within the spirit and scope of the present disclosure.

Operation of the embodiment of FIGS. 5A-5H is as follows. As the housing 252 of the closing device 200 is retracted from the percutaneous incision 219, as shown in FIG. 5C, the stowage detent 255 releases. The automatic driving assembly 260 and carrier tube 202 may remain stationary and therefore float relative to the housing 252. The procedure sheath 216 is retracted as the housing 252 is withdrawn, exposing the distal end portion 207 of the carrier tube 202. The automatic driving assembly 260 eventually contacts a stop (or, in some embodiments, the automatic driving assembly is fixed), and further retraction causes the automatic driving assembly 260 and carrier tube 202 to retract as well. As the automatic driving assembly 260 retracts, the suture 204, which is threaded through the anchor 208, unwinds from the spool assembly along a cam suture path and causes rotation of the spool assembly 266 and driving plate 264 with a variable rotation force.

As the driving plate 264 rotates, the coil 272 is advanced to drive and advance the compaction tube 212. In some arrangements, the coil 272 may be long enough and constructed such that the coil 272 functions as the compaction tube 212. The compaction tube 212 compacts the sealing plug 210. Therefore, as the closing device 200 is retracted from the percutaneous incision 219, the procedure sheath 216 may be retracted (see FIGS. 5E-5F), the carrier tube 202 may be retracted, and the sealing plug 210 is automatically compacted (see FIGS. 5G-5H). The sealing plug 210 is more likely to create a sufficient arterial seal without a gap relative to the anchor 208, as may otherwise occur with a separate manual compaction procedure.

Moreover, when the sealing plug 210 has been sufficiently compacted, the automatic driving assembly 260 may be disengaged, enabling further retraction of the closure device 200 without additional compaction. With the sealing plug 210 fully compacted, there may be little or no portion of the suture 204 extending outside of the tissue layer 230 and exposed to an operator. Therefore, it may be difficult for an operator to separate the sealing plug 210 and anchor 208 from the remainder of the closure device 200. In addition, too much retraction with the selectably automatic driving assembly 260 enabled could potentially overcompact the sealing plug 210 into the artery 228. Accordingly, the automatic driving assembly 260 may be advantageously disabled by activating the release member 270 through the release member opening 251. Activating the release member 270 allows the suture 204 to at least partially unwind from the spool assembly 266 without driving the compaction tube 212. Unwinding the spool assembly 266 exposes a sufficient length of the suture 204 to allow an operator to cut the suture 204 and separate the sealing plug 210 and anchor 208 from the remainder of the closure device 200.

The preceding description has been presented only to illustrate and describe exemplary embodiments of the present disclosure. It is not intended to be exhaustive or to limit the invention to any precise form disclosed. Many modifications and variations are possible in light of the above teaching. It is intended that the scope of the invention be defined by the following claims.

What is claimed is:
1. A tissue puncture closure device, comprising:
an anchor;
a sealing plug;
a suture attached to the anchor;
a compaction member assembly comprising a plate;
a spool assembly comprising a plurality of posts, the plurality of posts extending through the plate;
a release member operable to move the plurality of posts relative to the plate, the suture being spooled around the plurality of posts between the plate and the release member, wherein unspooling the suture from the plurality of posts drives the compaction member assembly to apply an axially directed compressive force to compact the sealing plug toward the anchor.
2. The tissue puncture closure device of claim 1, wherein the plate comprises a plurality of apertures, the plurality of posts extending through the plurality of apertures.
3. The tissue puncture closure device of claim 1, wherein the release member comprises a post contact surface in contact with at least one post of the plurality of posts.
4. The tissue puncture closure device of claim 1, wherein the plate comprises a surface facing the release member, the surface facing the release member being configured to contact the release member upon operation of the release member.

5. The tissue puncture closure device of claim 1, wherein the release member is operable to move axially along an axis extending longitudinally through the plate.
6. The tissue puncture closure device of claim 1, wherein the release member contacts a biasing member, the biasing member biasing the release member away from the plate.
7. The tissue puncture closure device of claim 1, wherein the plurality of posts comprises at least one connector post, the at least one connector post providing a connection between the plate and the spool assembly.
8. The tissue puncture closure device of claim 7, wherein the at least one connector post comprises at least one of as flexible arm, tab, protrusion, or lip extending through the plate.
9. The tissue puncture closure device of claim 1, wherein at least one of the plurality of posts provides a tactile feedback to an operator when the release member is operated.
10. A method of sealing a tissue puncture in an internal tissue wall of a vessel accessible through a percutaneous incision, the method comprising:
providing a closure device having an anchor, a sealing plug, a suture extending between the sealing plug and the anchor, a compaction member assembly, a release member, and a spool assembly having a plurality of posts, the suture being wound around the plurality of posts between the compaction member assembly and the release member;
inserting the anchor through the tissue puncture;
withdrawing the closure device from the tissue puncture with the anchor positioned within the vessel, wherein withdrawing the closure device rotates the spool assembly to drive the compaction member assembly to compact the sealing plug toward the anchor;
actuating the release member to release the suture from the plurality of posts.
11. The method of claim 10, wherein rotating the spool assembly applies a variable compaction force to the compaction member assembly.
12. The method of claim 10, wherein actuating the release member comprises moving the release member along a longitudinal axis extending through the release member and the compaction member assembly.
13. The method of claim 10, wherein actuating the release member comprises contacting the plurality of posts with the release member and moving the plurality of posts relative to the compaction member assembly using the release member.
14. The method of claim 10, wherein the plurality of posts comprises at least one connector post, the at least one connector post providing tactile feedback to an operator when the release member is actuated.
15. The method of claim 10, wherein the compaction member assembly comprises a plate and a compaction member wound around the plate, the compaction member unwinding from the plate upon rotation of the plate.
16. The method of claim 10, wherein withdrawing the closure device rotates the spool assembly by unwinding the suture from the plurality of posts.
17. A tissue puncture closure device, comprising:
an anchor;
a sealing plug;
a suture attached to the anchor;
a housing;
a compaction member assembly positioned in the housing, the compaction member assembly comprising a plate, the plate being rotatable relative to the housing;

a spool assembly comprising a plurality of posts, the plurality of posts extending through the plate, the spool assembly being translatable and rotatable relative to the housing;

a release member operable to move the plurality of posts relative to the plate, the suture being spooled around the plurality of posts, the release member being translatable and rotatable relative to the housing.

18. The tissue puncture closure device of claim 17, wherein the plate is not translatable relative to the housing.

19. The tissue puncture closure device of claim 17, wherein the spool assembly and release member are translatable along coincident central axes of rotation.

20. The tissue puncture closure device of claim 19, wherein a central axis of rotation of the compaction member assembly is coincident with the central axes of rotation of the spool assembly and the release member.

* * * * *